United States Patent [19]

Hechenbleikner et al.

[11] 4,456,567
[45] Jun. 26, 1984

[54] 3,9-DICHLORO-2,4,8,10-TETRAOXA-3,9-DIPHOSPHASPIRO [5,5] UNDECANE-9-OXIDE AND PROCESS FOR PREPARING SAME

[75] Inventors: Ingenuin Hechenbleikner, West Cornwall; William P. Enlow, Falls Village, both of Conn.

[73] Assignee: Borg-Warner Corporation, Chicago, Ill.

[21] Appl. No.: 511,126

[22] Filed: Jul. 6, 1983

Related U.S. Application Data

[63] Continuation-in-part of Ser. No. 321,858, Nov. 16, 1981, abandoned.

[51] Int. Cl.$^3$ .............................................. C07F 9/15
[52] U.S. Cl. ................................................... 260/985
[58] Field of Search ........................................ 260/985

[56] References Cited

U.S. PATENT DOCUMENTS 2,899,454  8/1959  McBee et al. ....................... 260/985
3,136,805  6/1964  Baranavckas et al. .............. 260/985
3,939,229  2/1976  Hechenbleikner et al. ......... 260/985

OTHER PUBLICATIONS

Lucas et al., "J. Am. Chem. Soc.", vol. 75, (1950), pp. 5491–5497.

Primary Examiner—J. E. Evans
Attorney, Agent, or Firm—Aubrey L. Burgess

[57] ABSTRACT

A process for preparing an asymmetrical pentaerythritol compound containing both trivalent and pentavalant phosphorus. The process involves merely bubbling oxygen into a solution containing 3,9-dichloro-2,4,8,10-tetraoxa-3,9-diphosphaspiro [5,5] undecane.

6 Claims, No Drawings

3,9-DICHLORO-2,4,8,10-TETRAOXA-3,9-DIPHOSPHASPIRO [5,5] UNDECANE-9-OXIDE AND PROCESS FOR PREPARING SAME

This application is a continuation-in-part of application Ser. No. 321,858, filed Nov. 16, 1981 now abandoned.

This invention relates as indicated to an asymmetrical pentaerythritol diphosphite and to a process for its preparation. More particularly it relates to an oxidation process which is selective in character.

BACKGROUND OF THE INVENTION

In the ordinary situation the two identical reactive groups of a bifunctional reactant are equally reactive. That is, they each will partake in a given reaction with the result that each is converted to something else. If the bifunctional reactant is symmetrical then the product of a reaction involving that reactant likewise will be symmetrical. For this reason the preparation of asymmetrical compounds, especially higher molecular weight compounds, frequently is difficult and correspondingly expensive.

U.S. Pat. No. 3,358,004 (Bliss et al.) shows the preparation of symmetrical azides having the following general formula:

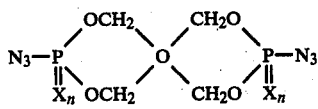

where x is oxygen or sulfur and n is an integer of 0 or 1. Such azides are prepared by reaction of an alkali metal azide with the corresponding 3,9-dichloro-2,4,8,10-tetraoxa-3,9-diphosphaspiro[5,5]undecane, or dioxide or disulfide thereof. In each case, however, the reactants and products are symmetrical.

Derwent Japanese Patent Report, 4 (37) 5:13 (Oct. 20, 1965) shows the reaction of a compound of the general formula:

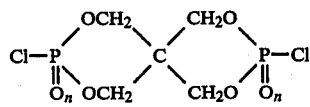

where "n is not defined", with a substituted or unsubstituted ethylene imine to form the expected symmetrical product.

SUMMARY OF THE INVENTION

The invention of this application is a process for preparing an asymmetrical pentaerythritol compound containing both trivalent and pentavalent phosphorus comprising oxidizing 3,9-dichloro-2,4,8,10-tetraoxa-3,9-diphosphospiro[5,5]undecane. The asymmetrical product generally is isolated as a solid which precipitates from the process mixture.

The reaction of the process is illustrated by the following equation:

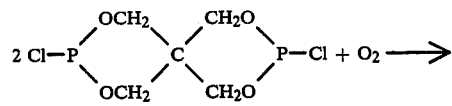

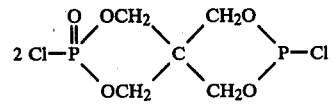

The 3,9-chloro-2,4,8,10-tetraoxa-3,9-diphosphaspiro[5,5]undecane starting material may be prepared by the method of Lucas et al., J. Am. Chem. Soc., 72, 5491,5495 (1950). One half mol of pentaerythritol is added with stirring to a solution of one mol of phosphorus trichloride in methylene chloride. The mixture is heated at reflux temperature until one hour after the last of the pentaerythritol has disappeared. Solvent then is removed and the residue is the desired product. It may be purified by crystallization from chloroform.

The oxidation reaction of the present process is carried out preferably with oxygen. The oxygen may be pure oxygen or it may be diluted with some other gaseous component, e.g., the oxidizing agent may be air. The process mixture must be dry. Care should be taken to insure the anhydrous nature of the reactants and solvent.

The process is carried out in a solvent. It facilitates temperature control of the process and better, more intimate mixing of the reactants. Moreover, the different solubilities of the starting material and product in various solvents simplifies the isolation of the product. Halogenated hydrocarbons are suitable solvents, including chloroform, methylene chloride, ethylene dichloride, chlorobenzene, and the like, although other types of solvents such as benzene, toluene, heptane, etc., i.e., hydrocarbons, are also contemplated.

The temperature of the reaction mixture is not critical although the reaction does, of course, proceed faster at higher temperatures. Temperatures within the range of from about 20° C. to about 70° C. are quite satisfactory. Higher or lower temperatures may be used in special situations, but ordinarily a temperature within the above range permits the process to be carried out most conveniently.

The oxidizing agent, which ordinarily is oxygen itself or air, is added portionwise to the 3,9-dichloro-2,4,8,10-tetraoxa-3,9-diphosphaspiro[5,5]undecane, which should be agitated during the addition. In the usual case, where oxygen or air is bubbled into the solution, that mode of addition will in itself provide suitable agitation. When no more oxygen is consumed the reaction is halted and the product mixture filtered at room temperature; the solid product is in most instances suitably pure for uses as an intermediate in the preparation of asymmetrical derivatives.

The process of the invention is especially useful because it yields asymmetrical products, i.e., products which contain both trivalent and pentavalent phosphorus. These are in turn useful as intermediates in the preparation of asymmetrical products which may contain a wide variety of phosphite and phosphate groups in the same molecule. The preparation of such products by prior art processes is difficult and quite inefficient.

An illustrative example of such an asymmetrical derivative is the distearyl derivative, i.e., having the structure

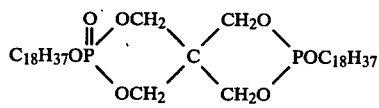

The above compound is effective at low concentrations, viz., from about 0.01 to about 0.5 percent, to impart thermal stability to polymer compositions. This is shown by data obtained from a multiple extrusion test wherein the test samples are extruded from a 24/1, L/D, ¾" C. W. Brabender extruder at 525° F. The compared samples contained (A) 100 parts of polypropylene, 0.10 part of tetrakis methylene 3-(3',5'-ditertiarybutyl-4'-hydroxyphenyl)propionate methane, and 0.05 part of calcium stearate, and (B) this same composition plus 0.05 part of the 0.05 part of the above distearyl derivative. The test is run by extruding each sample five times under the above conditions and noting the melt flow (grams/minute, per ASTMD-1238) after the first, third and fifth passes:

| Sample | MELT FLOW | | |
| --- | --- | --- | --- |
| | 1st Pass | 2nd Pass | 3rd Pass |
| A | 4.4 | 10.0 | 18.9 |
| B | 2.4 | 3.7 | 6.6 |

A specific embodiment of the process herein is shown in the following example.

EXAMPLE

Oxygen is bubbled into a solution of 96 grams (0.362 mol) of 3,9-dichloro-2,4,8,10-tetraoxa-3,9-diphosphaspiro[5,5]undecane (M.P., 121°–123° C.) in 385 ml. of chlorobenzene. The temperature of the solution is maintained throughout the addition within the range of 30°–40° C. When it appears that no more oxygen is being absorbed (after above five hours) the introduction of oxygen is halted and the product mixture is filtered. The solid product weighs 83 grams and melts at 170°–182° C. The residual presence of a phosphite group is shown by the decolorization of aprotic aqueous iodine, and IR analysis shows the presence of a P=O group.

All parts and percentages herein, unless otherwise expressly stated, are by weight.

I claim:

1. A process for preparing an asymmetrical pentaerythritol compound containing both trivalent and pentavalent phosphorus comprising oxidizing 3,9-dichloro-2,4,8,10-tetraoxa-3,9-diphosphaspiro[5,5]undecane, to form the 3,9-dichloro-3'-oxo-2,4,8,10-tetraoxa-3,9-diphosphaspiro[5,5]undecane in an anhydrous environment, and isolating said asymmetrical pentaerythritol compound.

2. The process of claim 1 wherein the oxidation is accomplished by means of oxygen.

3. The process of claim 1 wherein the oxidation is accomplished by bubbling oxygen through 3,9-dichloro-2,4,8,10-tetraoxa-3,9-diphosphaspiro[5,5]undecane.

4. The process of claim 3 wherein the oxidation is accomplished by bubbling oxygen through a solution of 3,9-dichloro-2,4,8,10-tetraoxa-3,9-diphosphaspiro[5,5]undecane.

5. The process of claim 4 wherein the solution is a solution in chlorobenzene.

6. The process of claim 1 wherein the oxidation is carried out at a temperature within the range of from about 10° C. to about 75° C.

* * * * *

UNITED STATES PATENT AND TRADEMARK OFFICE
CERTIFICATE OF CORRECTION

PATENT NO. : 4,456,567
DATED : June 26, 1984
INVENTOR(S) : Ingenuin Hechenbleikner et al.

It is certified that error appears in the above-identified patent and that said Letters Patent is hereby corrected as shown below:

On the title page, "Attorney, Agent, or Firm - Aubrey L. Burgess"

should read -- Attorney, Agent, or Firm - Robert L. Zieg --.

Signed and Sealed this

Twelfth Day of March 1985

[SEAL]

Attest:

DONALD J. QUIGG

Attesting Officer     Acting Commissioner of Patents and Trademarks